(12) United States Patent
Poly et al.

(10) Patent No.: US 9,328,389 B2
(45) Date of Patent: *May 3, 2016

(54) MULTIPLEX AMPLIFICATION REACTION METHOD FOR DETERMINATION OF CAMPYLOBACTER JEJUNI PENNER/CAPSULE TYPE

(71) Applicants: Federic Poly, Silver Spring, MD (US); Patricia Guerry, Silver Spring, MD (US); Craig Parker, Davis, CA (US)

(72) Inventors: Federic Poly, Silver Spring, MD (US); Patricia Guerry, Silver Spring, MD (US); Craig Parker, Davis, CA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/963,146

(22) Filed: Aug. 9, 2013

(65) Prior Publication Data
US 2015/0044682 A1 Feb. 12, 2015

(51) Int. Cl.
C12Q 1/68 (2006.01)
C12P 19/34 (2006.01)
C07H 21/04 (2006.01)

(52) U.S. Cl.
CPC ............ *C12Q 1/689* (2013.01); *C12Q 2600/16* (2013.01)

(58) Field of Classification Search
USPC .............................. 435/6.12, 91.2; 536/24.33
See application file for complete search history.

(56) References Cited

U.S. PATENT DOCUMENTS

| | | | |
|---|---|---|---|
| 8,530,166 B2 * | 9/2013 | Poly ..................... | C12Q 1/689 435/6.12 |
| 2006/0051752 A1 | 3/2006 | Wang | |
| 2008/0038742 A1 | 2/2008 | Porter | |

OTHER PUBLICATIONS

Parker et al. Journal of Clinical Microbiology, Jun. 2005, p. 2771-2781.*
Karlyshev et al. Analysis of Campylobacter jejuni capsular loci reveals multiple mechanisms for the generation of structural diversity and the ability to form complex heptoses. Mol Microbiol. 2005, vol. 55(1), p. 90-103. Abstract; p. 91, col. 1, para 2; p. 92, Fig 1 and Table 1; and p. 100, col. 2, para 2 and 4. Relevant to Claims 1-20.
Genbank_AL111168, Campylobacter jejuni subsp. jejuni NCTC 11168 complete genome, May 13, 2009, [online]. [Retrieved on Apr. 7, 2011]. Retrieved from the Internet: <URL: http://www.ncbi.nlm.nih.gov/nuccore/AL111168> Entire document, especially Definition; and complement(1373947..1374810)/locus_tag="Cj1437c" Relevant to Claims 4, 10, 13, 16-17.
Genbank_BX545859, Campylobacter jejuni, Apr. 17, 2005, [online]. [Retrieved on Apr. 6, 2011]. Retrieved from the Internet: <URL: http://www.ncbi.nlm.nih.gov/nuccore/BX545859> Entire document, especially Definition; and gene complement (9304..11844)/locus_tag="HS1.08" Relevant to Claims 13,17.
McNally et al. Commonality and Biosynthesis of teh o-Methyl Phosphoramidate Capsule Modification in Campylobacter jejuni. J Biol Chem. 2007, vol. 282(39), p. 28566-76. Abstract. Relevant to Claims 1-20.
Poly et al. Discrimination of major capsular types of Campylobacter jejuni by multiplex PCR.J Clin Microbiol. Mar 16, 2011. [Epub ahead of print] PDF file: p. 1-31, Entire document. Relevant to Claims 1-20.
Rachlin, et al., MuPlex: multi-objective multiplex PCR assay design. Nucleic Acids Research, 2005, vol. 33: W544-W547. Relevant to Claims 1-20.
Vallone and Butler, AutoDimer: a screening tool for primer-dimer and hairpin structures, Biotechniques, 2004, vol. 37: 226-231. Relevant to Claims 1-20.

* cited by examiner

*Primary Examiner* — Kenneth R. Horlick
*Assistant Examiner* — Joyce Tung
(74) *Attorney, Agent, or Firm* — Albert M. Churilla; Ning Yang; Diane Tso

(57) ABSTRACT

The inventive method and associated reagents relate to a molecular approach to determining *Campylobacter jejuni* capsule/Penner types. The invention also relates to a method of identifying *Campylobacter jejuni* types using primers in a multiplex PCR assay.

12 Claims, 2 Drawing Sheets

SEQUENCE LISTING

<160> NUMBER OF SEQ ID NOS: 69

<210> SEQ ID NO 1
<211> LENGTH: 20
<212> TYPE: DNA
<213> ORGANISM: Campylobacter jejuni

```
<400> SEQUENCE: 1
cgaggatgaa aatgcctcaa                                                    20

<210> SEQ ID NO 2
<211> LENGTH: 23
<212> TYPE: DNA
<213> ORGANISM: Campylobacter jejuni

<400> SEQUENCE: 2
ggcaacaaac aaacatattc aga                                                23

<210> SEQ ID NO 3
<211> LENGTH: 25
<212> TYPE: DNA
<213> ORGANISM: Campylobacter jejuni

<400> SEQUENCE: 3
aaatttgttt ttcatatttt tacgg                                              25

<210> SEQ ID NO 4
<211> LENGTH: 20
<212> TYPE: DNA
<213> ORGANISM: Campylobacter jejuni

<400> SEQUENCE: 4
ttaggtgcgg ttaccaaagg                                                    20

<210> SEQ ID NO 5
<211> LENGTH: 20
<212> TYPE: DNA
<213> ORGANISM: Campylobacter jejuni

<400> SEQUENCE: 5
gtagcggatc agcagcatta                                                    20

<210> SEQ ID NO 6
<211> LENGTH: 25
<212> TYPE: DNA
<213> ORGANISM: Campylobacter jejuni

<400> SEQUENCE: 6
catcaaaatc atcttttaac accaa                                              25

<210> SEQ ID NO 7
<211> LENGTH: 23
<212> TYPE: DNA
<213> ORGANISM: Campylobacter jejuni

<400> SEQUENCE: 7
ggggtaaaat agccaatatt cca                                                23

<210> SEQ ID NO 8
<211> LENGTH: 23
<212> TYPE: DNA
<213> ORGANISM: Campylobacter jejuni

<400> SEQUENCE: 8
ccaacaagcc atatttgttt ttc                                                23

<210> SEQ ID NO 9
<211> LENGTH: 25
<212> TYPE: DNA
<213> ORGANISM: Campylobacter jejuni
```

<400> SEQUENCE: 9
ggaggtaaaa cgatattctc cttaa　　　　　　　　　　　　　　　　　25

<210> SEQ ID NO 10
<211> LENGTH: 23
<212> TYPE: DNA
<213> ORGANISM: Campylobacter jejuni

<400> SEQUENCE: 10
tgaagatttt gaatggatgt gtg　　　　　　　　　　　　　　　　　23

<210> SEQ ID NO 11
<211> LENGTH: 26
<212> TYPE: DNA
<213> ORGANISM: Campylobacter jejuni

<400> SEQUENCE: 11
gaataaatat tgcttccata ctttca　　　　　　　　　　　　　　　　26

<210> SEQ ID NO 12
<211> LENGTH: 21
<212> TYPE: DNA
<213> ORGANISM: Campylobacter jejuni

<400> SEQUENCE: 12
gcaaaatgag aatctccacc a　　　　　　　　　　　　　　　　　　21

<210> SEQ ID NO 13
<211> LENGTH: 21
<212> TYPE: DNA
<213> ORGANISM: Campylobacter jejuni

<400> SEQUENCE: 13
tggatgggat attgatgaca a　　　　　　　　　　　　　　　　　　21

<210> SEQ ID NO 14
<211> LENGTH: 20
<212> TYPE: DNA
<213> ORGANISM: Campylobacter jejuni

<400> SEQUENCE: 14
ccctggaaga gtatgggaca　　　　　　　　　　　　　　　　　　　20

<210> SEQ ID NO 15
<211> LENGTH: 23
<212> TYPE: DNA
<213> ORGANISM: Campylobacter jejuni

<400> SEQUENCE: 15
ggcaaagagc tttattttgt tga　　　　　　　　　　　　　　　　　23

<210> SEQ ID NO 16
<211> LENGTH: 21
<212> TYPE: DNA
<213> ORGANISM: Campylobacter jejuni

<400> SEQUENCE: 16
gccgtagcaa catcaaatac a　　　　　　　　　　　　　　　　　　21

<210> SEQ ID NO 17
<211> LENGTH: 24
<212> TYPE: DNA
<213> ORGANISM: Campylobacter jejuni -continued

<400> SEQUENCE: 17
gatgtcaatt ctcaggatta tgaa                                              24

<210> SEQ ID NO 18
<211> LENGTH: 24
<212> TYPE: DNA
<213> ORGANISM: Campylobacter jejuni

<400> SEQUENCE: 18
gctcttttga ggtatctacg gaat                                              24

<210> SEQ ID NO 19
<211> LENGTH: 20
<212> TYPE: DNA
<213> ORGANISM: Campylobacter jejuni

<400> SEQUENCE: 19
tccacttggg atgaaaagga                                                   20

<210> SEQ ID NO 20
<211> LENGTH: 20
<212> TYPE: DNA
<213> ORGANISM: Campylobacter jejuni

<400> SEQUENCE: 20
accgcatact ttgagcctgt                                                   20

<210> SEQ ID NO 21
<211> LENGTH: 23
<212> TYPE: DNA
<213> ORGANISM: Campylobacter jejuni

<400> SEQUENCE: 21
cccatattta aacaatggag tga                                               23

<210> SEQ ID NO 22
<211> LENGTH: 26
<212> TYPE: DNA
<213> ORGANISM: Campylobacter jejuni

<400> SEQUENCE: 22
tcatactttg aaaaacatta tctgga                                            26

<210> SEQ ID NO 23
<211> LENGTH: 20
<212> TYPE: DNA
<213> ORGANISM: Campylobacter jejuni

<400> SEQUENCE: 23
tcatggagct ggaacaacag                                                   20

<210> SEQ ID NO 24
<211> LENGTH: 21
<212> TYPE: DNA
<213> ORGANISM: Campylobacter jejuni

<400> SEQUENCE: 24
gctggaactt cttttgcaat c                                                 21

<210> SEQ ID NO 25
<211> LENGTH: 27
<212> TYPE: DNA
<213> ORGANISM: Campylobacter jejuni

```
<400> SEQUENCE: 25
aaaactatta gcttgatttt accttgg                                        27

<210> SEQ ID NO 26
<211> LENGTH: 20
<212> TYPE: DNA
<213> ORGANISM: Campylobacter jejuni

<400> SEQUENCE: 26
gcgaaagacg gattgttcat                                                20

<210> SEQ ID NO 27
<211> LENGTH: 20
<212> TYPE: DNA
<213> ORGANISM: Campylobacter jejuni

<400> SEQUENCE: 27
tggatgaagg ggacttatgg                                                20

<210> SEQ ID NO 28
<211> LENGTH: 20
<212> TYPE: DNA
<213> ORGANISM: Campylobacter jejuni

<400> SEQUENCE: 28
tggtttgaag agcatcagca                                                20

<210> SEQ ID NO 29
<211> LENGTH: 24
<212> TYPE: DNA
<213> ORGANISM: Campylobacter jejuni

<400> SEQUENCE: 29
cagctataaa tcatgggtat tgga                                           24

<210> SEQ ID NO 30
<211> LENGTH: 25
<212> TYPE: DNA
<213> ORGANISM: Campylobacter jejuni

<400> SEQUENCE: 30
gtaatcaata cattttcct tgctt                                           25

<210> SEQ ID NO 31
<211> LENGTH: 26
<212> TYPE: DNA
<213> ORGANISM: Campylobacter jejuni

<400> SEQUENCE: 31
tccggaaaaa ttttatttag attctc                                         26

<210> SEQ ID NO 32
<211> LENGTH: 25
<212> TYPE: DNA
<213> ORGANISM: Campylobacter jejuni

<400> SEQUENCE: 32
aacaatacca ggataccaat cttca                                          25

<210> SEQ ID NO 33
<211> LENGTH: 25
<212> TYPE: DNA
<213> ORGANISM: Campylobacter jejuni
```

<400> SEQUENCE: 33
aaaacacgct attaatcatg gtgac                                    25

<210> SEQ ID NO 34
<211> LENGTH: 26
<212> TYPE: DNA
<213> ORGANISM: Campylobacter jejuni

<400> SEQUENCE: 34
atgtaggcca agttatacaa cctttt                                   26

<210> SEQ ID NO 35
<211> LENGTH: 26
<212> TYPE: DNA
<213> ORGANISM: Campylobacter jejuni

<400> SEQUENCE: 35
gaaatcattt ttatgatatt gtggtt                                   26

<210> SEQ ID NO 36
<211> LENGTH: 24
<212> TYPE: DNA
<213> ORGANISM: Campylobacter jejuni

<400> SEQUENCE: 36
tcacagtcac aataaatagc caaa                                     24

<210> SEQ ID NO 37
<211> LENGTH: 20
<212> TYPE: DNA
<213> ORGANISM: Campylobacter jejuni

<400> SEQUENCE: 37
gagatggtgg tggtcatcaa                                          20

<210> SEQ ID NO 38
<211> LENGTH: 20
<212> TYPE: DNA
<213> ORGANISM: Campylobacter jejuni

<400> SEQUENCE: 38
acgttgcaac caatcctttg                                          20

<210> SEQ ID NO 39
<211> LENGTH: 19
<212> TYPE: DNA
<213> ORGANISM: Campylobacter jejuni

<400> SEQUENCE: 39
gcataccaga tggctttgg                                           19

<210> SEQ ID NO 40
<211> LENGTH: 21
<212> TYPE: DNA
<213> ORGANISM: Campylobacter jejuni

<400> SEQUENCE: 40
aatgcagcgt gcttcttatt t                                        21

<210> SEQ ID NO 41
<211> LENGTH: 22
<212> TYPE: DNA
<213> ORGANISM: Campylobacter jejuni

<400> SEQUENCE: 41
gaattggaca taaccacgga at                                          22

<210> SEQ ID NO 42
<211> LENGTH: 22
<212> TYPE: DNA
<213> ORGANISM: Campylobacter jejuni

<400> SEQUENCE: 42
atgcaaagtg cacatattct cc                                          22

<210> SEQ ID NO 43
<211> LENGTH: 23
<212> TYPE: DNA
<213> ORGANISM: Campylobacter jejuni

<400> SEQUENCE: 43
caacccttgg atgacaatag aga                                         23

<210> SEQ ID NO 44
<211> LENGTH: 23
<212> TYPE: DNA
<213> ORGANISM: Campylobacter jejuni

<400> SEQUENCE: 44
accgtcaata tcatcaggat tta                                         23

<210> SEQ ID NO 45
<211> LENGTH: 20
<212> TYPE: DNA
<213> ORGANISM: Campylobacter jejuni

<400> SEQUENCE: 45
gccgcaggag ataatgaaga                                             20

<210> SEQ ID NO 46
<211> LENGTH: 22
<212> TYPE: DNA
<213> ORGANISM: Campylobacter jejuni

<400> SEQUENCE: 46
tttgccdttt agatcttgag ga                                          22

<210> SEQ ID NO 47
<211> LENGTH: 450
<212> TYPE: DNA
<213> ORGANISM: Campylobacter jejuni

<400> SEQUENCE: 47
cgaggatgaa aatgcctcaa agtattactc tcttattcca ccatgtagaa gtatttgtct    60 tgtagggat cctatttctt ctttaagatc tcatgttgga ggtaaaagac atggtgttaa    120
ttatttaaat attgtagatt ttggcactaa tattgaatgc gttatgagca acaggattgg   180
atatgctaat attggattta attcacattt tccctgtgtt gatatttcag aagcatttat   240
tgataacaaa tttatgtgtt ttcatgattc tttattatgg aaatttttaa aacaagataa   300
aatttatttt ttagatacaa atgcaatttt gggcaacaaa tgttttgaaa gtattaaact   360
aatctctgaa tattttaatt ttaatccacc aaaatatagc gatatgaaat tctatgaagg   420
aaaaatttct gaatatgttt gtttgttgcc                                   450

<210> SEQ ID NO 48
<211> LENGTH: 522
<212> TYPE: DNA
<213> ORGANISM: Campylobacter jejuni

<400> SEQUENCE: 48

```
aaatttgttt ttcatatttt tacggaaaat tgtactgttt aataacaaga taaaatcaat      60
aaaactatca atgaattaaa tcaaatttat ccttgtgaaa ttttccttca ttttgtcgag     120
attgatgaat ttaaaaattt ttctagggta ccttggagta atcatgcagc aatgttttat     180
aaaattcagg ctccgaaaat tttacatgat atagataaaa ttttattttt aggtgctgat     240
acattgtgcg ttgatgatat tagagagctt ttcgatttag atttaaaaga taatattatt     300
gtcgctgctt gggattgttg taattatcaa gggtatgtta gacgtgtttc ttgcaatgat     360
ttgtctagag aagatttgat attttatgat agttattatt gtataaacaa cgatgtaatg     420
ttaattaatg ttaaagagtg gttaaaaaat aatatagaag aaaaatgtgc ttattattta     480
actaattatt ttagatgtat ttcctttggt aaccgcacct aa                        522
```

<210> SEQ ID NO 49
<211> LENGTH: 819
<212> TYPE: DNA
<213> ORGANISM: Campylobacter jejuni

<400> SEQUENCE: 49

```
gtagcggatc agcagcatta tacccctttt tgacttttg tggaataact tctaaagcct       60
atccttggac aggtaaaaat agtatgtatt tatctatgta taattataaa aacgattgct     120
atcctataca aattgctcca tgtgcaaaag atagtgaatt atttccagag aatcataaat     180
tattacattt attagatagc aagattacat tgtttttgt tatgagagat cctatatcta     240
taataaaatc tggtataaat cacattgatt tacgcaatac tattcctagt aattttaaaa     300
gaaaattcaa tatagtagat aattttaaag atatttttcc agtaataaaa tatccatatt     360
ataaaaatca agaaaaacct aatttgaatt attttgataa gataattgaa gattgtaaaa     420
aattctatt tacattaggt gatattctaa atttagataa tacaaataga gatattgttt     480
gtatcaattt taatgattta tctaaagata gatgttatga tacatttaaa tatttatcaa     540
gtaagtttgg atttgatata aataaaataa ataaaacaat tgttctggt agaatcggta     600
aagaatcagg tcagatgtgt tatttgccaa taattataaa ttgtagtggt caaattttaa     660
aacaatattt aaatttaaaa gttgaatcag atattaatat tttgattaca acatatcaat     720
tatgtaaaaa tatttatgct tacgagaaca taacaaatga atttgataat ataatatatg     780
ataatataat tatttggtg ttaaaagatg attttgatg                             819
```

<210> SEQ ID NO 50
<211> LENGTH: 100
<212> TYPE: DNA
<213> ORGANISM: Campylobacter jejuni

<400> SEQUENCE: 50

```
ggggtaaaat agccaatatt ccagagatac tattaagata tagaaggcat tctagaagta      60
ttactagcac ttttagtgaa aaacaaatat ggcttgttgg                            100
```

<210> SEQ ID NO 51
<211> LENGTH: 201
<212> TYPE: DNA
<213> ORGANISM: Campylobacter jejuni

<400> SEQUENCE: 51

```
tgaagatttt gaatggatgt gtgaaaatat gataggagat gacactgggg ataacatatc    60
tcatttaaat cgctatttaa atgaactaac gggaatttat tgggcttgga aaaattatga   120
taaattaggt aatcctgatt atataggata tgagcattat agaagacatt ttattttaa    180
ggagaatatc gttttacctc c                                             201
```

<210> SEQ ID NO 52
<211> LENGTH: 280
<212> TYPE: DNA
<213> ORGANISM: Campylobacter jejuni

<400> SEQUENCE: 52

```
gaataaatat tgcttccata ctttcaaata ttaaattttt tgaaaaaggt gaaggtgtaa    60
atttatattt ttataaaaat aattatgcta tcaatttacc ttcttttgaa gataagccta   120
aaattgcagt ttgcctatgg gggattttta gaggtaacta tattaaagct ctagatgata   180
taaataagct aatagttaag cctttaaatg ctgatttatt tatacatact tggaatgaat   240
gtcatatttg gtctggatat ggtggagatt ctcattttgc                         280
```

<210> SEQ ID NO 53
<211> LENGTH: 801
<212> TYPE: DNA
<213> ORGANISM: Campylobacter jejuni

<400> SEQUENCE: 53

```
tggatgggat attgatgaca attttactta cgggagctac aggatttata gggacgaatt    60
ttattttaca actctataaa aaatataata ttattgcttt agtaagaaaa tctagtaata   120
taagtagaat agaaaaattt tgtaaaattt actattatga agatataaat tctttaagga   180
atattctttt acaagaaaaa attcatggtg ttattcattt ggcaactctt tatttaaaaa   240
atcataagtc gcatcaaatt aacaatctgg taaatgccaa cattactttt ggtgctgaaa   300
ttttggaagt tttatatatg atggattata aaggatggtt tatcaacaca ggaacttttt   360
ggcagtttta taaaaatatt ccaaataatc ctttaaattt gtatgctgct acaaaaactg   420
ctttttttaag aatagttgat tattatgtgc aagttagcga aattaaattt accactatct   480
tattaaatga tacttatgga gctaatgatt ggcgtcaaaa aattttttaat ttatggttaa   540
attcttaaa aactcaagat gcaatcagta tgagttttgg agagcaagct atagatatgc   600
tttatgtaga tgatgttata aatgcttttg aagtttgtat ttcattgttt aattctgaga   660
attcagtttt attagaaaat agattattta ctttgcattc aaaagagagg aaaactttaa   720
gagaacttgc tgtaattttt gaaaattgta tagggaggaa acttaatatc atttgggggg   780
ctgtcccata ctcttccagg g                                             801
```

<210> SEQ ID NO 54
<211> LENGTH: 857
<212> TYPE: DNA
<213> ORGANISM: Campylobacter jejuni

<400> SEQUENCE: 54

```
gccgtagcaa catcaaatac atctatatat tctcttttg tttcacccttt ggtaaataat    60
gtaatttgag attttttat tgctgagcgg ataaaatcca tataaactct attatcatta   120
atttgtgccg ttggaccaat agcctgtgtt aatctcacta tagcagtact caatgagtat   180
ttttttgagt atgaatgaac cataaattca ctaatttgtt tggctaaagg atatgaattt   240
```

| | |
|---|---|
| ctaatattag taacactgaa ttttcctata tcatcttcaa caatgttatc acctattaca | 300 |
| tctccataaa tttccattgt tgataaaaat ataattttt caacattatt tttctttgag | 360 |
| aaatctagaa tatttttagt attagtatat ataatatcta cagtatctat aggattttca | 420 |
| ataaaaaaat cactttgcgt aggtgctgca caatggataa caatatcaat cttatcttgt | 480 |
| attttatata aatcttcata tatcaatc ttatctatat caccacaaat ttcttgaaaa | 540 |
| cgatcaatca tcttatcttt gtttctaaca agacaatata attttgcatt accatgcaaa | 600 |
| attaaagtca aaattgaacc tatatagcca tttgctccgg tgataagtat ttttttattt | 660 |
| gctattttat taatatgagt tccaaaatta tttttttaata gttcaatct ttttttttaaa | 720 |
| atttcattca tactttacac cccaaaaata ctttcaattg tttgcgcttg cattaatgct | 780 |
| tgaaccatat aaaaatcttt tggtgttgtt agctttatat tattatttga acactcaaca | 840 |
| aaataaagct ctttgcc | 857 |

<210> SEQ ID NO 55
<211> LENGTH: 82
<212> TYPE: DNA
<213> ORGANISM: Campylobacter jejuni

<400> SEQUENCE: 55

| | |
|---|---|
| gatgtcaatt ctcaggatta tgaaattgat atatttatac atacttggga taaatataat | 60 |
| tccgtagata cctcaaaaga gc | 82 |

<210> SEQ ID NO 56
<211> LENGTH: 128
<212> TYPE: DNA
<213> ORGANISM: Campylobacter jejuni

<400> SEQUENCE: 56

| | |
|---|---|
| tccacttggg atgaaaagga attacaagca atacaagatg ttatcaaaag cgatatgttt | 60 |
| actatgggta aaaaggtggc tgaatttgaa aaagattttg ctaaatttac aggctcaaag | 120 |
| tatgcggt | 128 |

<210> SEQ ID NO 57
<211> LENGTH: 185
<212> TYPE: DNA
<213> ORGANISM: Campylobacter jejuni

<400> SEQUENCE: 57

| | |
|---|---|
| cccatattta acaatggag tgatttgtta taaaaatgtt ccagatatta ccgcagctga | 60 |
| aatatttatt aatggtagta aatatgttaa ttatgattat tcaaagattg ctaatatttg | 120 |
| tagaaataat acatactatt ttgatgcttc agaaatagat ccagataatg ttttttcaaag | 180 |
| tatga | 185 |

<210> SEQ ID NO 58
<211> LENGTH: 216
<212> TYPE: DNA
<213> ORGANISM: Campylobacter jejuni

<400> SEQUENCE: 58

| | |
|---|---|
| tcatggagct ggaacaacag ctatgactta ttatttgaga ttgtgtagta tagagatgaa | 60 |
| tagatattat ggcgatccta tttatcagta tttagattca tataaaaggt tattgataaa | 120 |
| aacatcttat aatgtacttg cattagctgg aagagattat ggtatgaaaa aagagataaa | 180 |
| aaaattttat tcattgattg caaaagaagt tccagc | 216 |

```
<210> SEQ ID NO 59
<211> LENGTH: 278
<212> TYPE: DNA
<213> ORGANISM: Campylobacter jejuni

<400> SEQUENCE: 59
aaaactatta gcttgatttt accttggtct aattataaat attataaata tataaacaac    60
attcataaaa agttaagcat gaaatttgga tttaatgtga tcgatatgca agaatattat   120 gaaaaaata atttagaaga atttggacag ttaaaagatg gtgctcatca attcgacttt    180
attatgcaag agcttggaaa aaatattatt gctaatattc ataattttaa aaagcctaaa   240
aataatacta attttccaat gaacaatccg tctttcgc                           278

<210> SEQ ID NO 60
<211> LENGTH: 541
<212> TYPE: DNA
<213> ORGANISM: Campylobacter jejuni

<400> SEQUENCE: 60
tggatgaagg ggacttatgg aaaagctggt agtatagatt ataataaaaa ttggcgcaat    60
tataaaaaca atcaggcgg tggtatactt atagaccaag gaattcatat gcttgatttg   120
atgcgttatt tatctggtga ggagtttgaa aaaattaata gttttgtaac aaatgcttat   180
tgggatattg aagtggagga taatgcattt gctattatga aaacatattc aaatactata   240
gcaatgttgc attctagtgc tacacattgg aagcataagt ttttattaga gatgtatttt   300
gaagaaggtt atatcaatct tgatggtatt ttatctggga ctagaagtta tgcaccagaa   360
acattagttg tgggaagaag agaattcgaa gatataactt tgcaatggg taaacctaaa    420 gaaaatatta cttggtttga aaacgatgat tcttgggaaa ttgaaataaa agaattttta   480
gatgcagtgg acggtaaagt gagtgttaaa aatggcacta gtgctgatgc tcttcaaacc   540
a                                                                  541

<210> SEQ ID NO 61
<211> LENGTH: 653
<212> TYPE: DNA
<213> ORGANISM: Campylobacter jejuni

<400> SEQUENCE: 61
cagctataaa tcatgggtat tggaaaaatt taaatcaaaa agattttgat ttaattagtg    60
ttgatgatga tatagataaa gttttagatc gtataagata tgtaaaaaaa catgatatga   120 aaataatca tatagaatgg tctgatgaac ctactttgga tatgattgat agtatattgg    180
ataatcattg ttttaaatat aatacgattc ttaaaaagac aaatttagca ataaattatg   240
tagatatgaa acaaatatct gaagaatatg catttgaaac cttgcaagga ttagcagaaa   300
aatttaaatt aacacaacca aatgaagctg atagacacat tattagtatg aaacaaaata   360
atatttttag atatttactg ccattagtat taagaattaa taaaattgat attttttatta  420 ttggttctag tttgcatgtt tcacctagat ataagattat aaatcaccta gtgttagatt   480
ttgataatcc attttacgat ttattatttta tatcaattaa taaagaacaa atgttgagta   540
atgatttgat tatttttta aaacaatata tgtttaattt tacaattgcc ttggataaaa    600
aagtgaaatt tttacaatct aatttattaa gcaaggaaaa atgtattgat tac          653
```

```
<210> SEQ ID NO 62
<211> LENGTH: 85
<212> TYPE: DNA
<213> ORGANISM: Campylobacter jejuni

<400> SEQUENCE: 62
tccggaaaaa tttattttag attctccgtt aaatttaaat ttttataaat ataaatgtat      60
tgaagattgg tatcctggta ttgtt                                           85

<210> SEQ ID NO 63
<211> LENGTH: 170
<212> TYPE: DNA
<213> ORGANISM: Campylobacter jejuni

<400> SEQUENCE: 63
aaaacacgct attaatcatg gtgactataa atatgactac caaagatttg atgaaaacat      60
agatactaga aaatctatag aagatgaaat aaatagatca ttttattttt ttgatgataa     120
aaattgtaat tttatgatt ttgtaaaagg ttgtataact tggcctacat                 170

<210> SEQ ID NO 64
<211> LENGTH: 242
<212> TYPE: DNA
<213> ORGANISM: Campylobacter jejuni

<400> SEQUENCE: 64
agaaatcatt tttatgatat tgtggtttta tatgaacaac tacaagaata taaaattaat      60
aaaattattt ctatatatga agataataat ttcagtattc gctttttaa aattagtgaa     120 tatataaaaa atatgcgtac ttatttatat acttgtgatc attttcaat tgccaattat     180 tatcggattt taataccaaa tttattaagt gattataatt tggctattta ttgtgactgt     240
ga                                                                   242

<210> SEQ ID NO 65
<211> LENGTH: 341
<212> TYPE: DNA
<213> ORGANISM: Campylobacter jejuni

<400> SEQUENCE: 65
gagatggtgg tggtcatcaa tttgacttta aatgagaga gctaggcaaa aatataatat      60
ttcattatga aaactaaaa gattccgata tttcttttga tgaaattgat aacgtaaaat     120
atgattttaa aatatgttat tcaaatgagc ttgttggtaa caaaaataat aaaataataa     180
atttatcaaa ttctaaatat aatgaaaata ttgttagatt taatattggg gattctatta     240
aatttccaaa agcatatacg ggttacacaa ttataggtat acatcatgg aatacctcta     300 aaaatactca acttaattta ccaaaggatt ggttgcaacg t                         341

<210> SEQ ID NO 66
<211> LENGTH: 420
<212> TYPE: DNA
<213> ORGANISM: Campylobacter jejuni

<400> SEQUENCE: 66
gcataccaga tggctttggt atgcacttga taaatctgta agttttat ttggcttatga      60 aattattata agagagattt ataagggaa taaggtaatt ttatttggag atgatccgac     120
aactaatatt atttaaaag actatattaa caattcttac agtaattcca acgtatatac     180
aattgatgat tttatggatt tttcaaatat aaattgcgat caaagagttt tatttgaaat     240
```

```
agttttatg tccaatgcta agacaattta ctcaggaaat tctggatttt ccagagtggc        300
atattttata ggaaactcaa attttacct tattaatcat tattttactc accaagaaaa        360
aaaggaaatt atttacaaaa atttagataa attgccaata aataagaagc acgctgcatt       420
```

<210> SEQ ID NO 67
<211> LENGTH: 540
<212> TYPE: DNA
<213> ORGANISM: Campylobacter jejuni

<400> SEQUENCE: 67

```
gaattggaca taaccacgga ataatggctg atactgcatt attgtttttt tataatagat         60
gttataaaaa taatatattt ttattgccaa tattatatag gtcttatatt acttttgta        120 tgatgtggaa tattttggga gaacaaagg aacattctat tggatatcaa gaatttaatt        180
taaaacaaac tttaatatat ttaaaagaac taaatacgtt tttaataaa aataataata        240 aattatacgc tttatttggt tattttttta acaaaaaact aataacatca aagcttttaa        300
aagaaacaag caggaaattt ttaggattca tgttgaccaa taaaaaatta tattttccaa       360
taggtgatag cataagagag ccatctgttg aattttatc taaaatcttt tttccaaata       420
aaaaaataat ggatataaac gaaattctct atccgtattc tgttatgaat ggtagttatt      480
caagtgaatc ttatttcata taggaatg attcttttgg agaatatgtg cactttgcat       540
```

<210> SEQ ID NO 68
<211> LENGTH: 636
<212> TYPE: DNA
<213> ORGANISM: Campylobacter jejuni

<400> SEQUENCE: 68

```
caaccettgg atgacaatag agatagaata attgtttcaa aagcgcatgg ttctatttgt         60
ttgtatccca tattagctga tttaggatttt ttttctttc aaaatttaat gactataggg       120 caaaaaatt cattttaggg aactattccc gagcctacaa ttccaggata tgaaacaatc        180
aatggatctt taggacatgg tttaggtctt gcatgtggta gtgctatggc attacaaaaa       240
ttgaataaaa aaaataaagt tgttgtagta tgtggagatg gtgagttaaa tgaaggttcg       300
gtatgggagg caattatgtt tgctggtcat cacaagctta ataatttact attaattata      360
gattttaaca aagcttcaat gttgggattt gtaaggata ttattgattt aaatccaattt      420 aaagataaat ttaaggtgtt taattgggag gtatttgaaa taaaaatgg tcacaatatt       480 aaagagagtt ataagttttt agaagaggca attaatttta acgctgaaaa gcctaaagta       540
gttatttcac atactattaa aggaaatggg attaaaaact tagaaaataa tcctttgagt      600 catgtttgt ctataaatcc tgatgatatt gacggt                                636
```

<210> SEQ ID NO 69
<211> LENGTH: 741
<212> TYPE: DNA
<213> ORGANISM: Campylobacter jejuni

<400> SEQUENCE: 69

```
gccgcaggag ataatgaaga tttaaaactt ccatcgtgct ttaatttgac agttggagca         60
atcactttat tagaatatca tactcgaata ttacgacttt taggttttaa tgaaaaagat       120 attttttatta ttaaaaacca aaaagatatg gatttaaatt taaatttat aaatttgatt       180 aatattgaaa aaaataataa aaagagtttt ttatctttaa aatatttat cgattgctgt       240 cgagatttag aggatttgct tattataaac ggaaattctt tttttgaatt aaaagacttg      300
```

-continued

```
gagaaattaa ttaataaccc agaagaatcc aaggtgctaa tagaaaaaag aaatagtctt      360
tacacaaaag gcatagagct gattttggaa aataataaat tagtagcagt aagcgatcaa      420
attccaaaaa ttataccttg gttaagttat tatggtgcca tgttttttaac tagggttgat    480 gttttgaaag ttaaaaattt taataaagtg attaatgagc cttatttaaa tgtaatggta      540
aataatattg gaattaattt agaaaaagtc gatgtaaata ttcaaaataa taacacaaaa      600
acattggaac ttgtgggtgg ttcatttgct gggttgaata aaataaacat agtaaaaaaa      660
tatgcaaata tcgaaggtaa tgataaatta attatggaaa ttgaatggtt gaaaaatctt      720
cctcaagatc taaaaggcaa a                                                 741
```

MULTIPLEX AMPLIFICATION REACTION METHOD FOR DETERMINATION OF CAMPYLOBACTER JEJUNI PENNER/CAPSULE TYPE

CROSS-REFERENCES TO RELATED APPLICATIONS

This application is a Continuation-in-Part of U.S. nonprovisional application Ser. No. 13/031,718, filed 22 Feb. 2011, which claims the benefit of U.S. Provisional Application No. 61/307,632, filed 24 Feb. 2010, which are incorporated by reference, herein.

BACKGROUND OF INVENTION

1. Field of Invention

The inventive subject matter relates to a molecular method for determining *Campylobacter jejuni* capsule/Penner types.

2. Background

*Campylobacter* is a major cause of human bacterial diarrheal disease worldwide, with *C. jejuni*, and to a lesser extent *C. coli*, the most important pathogenic *Campylobacter* species. Campylobacteriosis symptoms range from asymptomatic infection to bloody diarrhea associated with abdominal pain and fever. The major source of human infection is through consumption of uncooked poultry, which is commonly colonized by *C. jejuni*. Post infectious sequelae associated with *C. jejuni* include reactive arthtitis, Guillain-Barré syndrome and irritable bowel syndrome.

The molecular pathogenesis of *C. jejuni* is not well understood, but a polysaccharide capsule (CPS) is one of the few recognized virulence determinants of this pathogen. The capsular polysaccharide undergoes a reversible phase variation in expression (Bacon, et al., Mol. Microbiol. 40:769-777 (2001)). The capsule contributes to serum resistance of *C. jejuni*, the ability of *C. jejuni* to invade intestinal epithelial cells in vitro, and, in a ferret model, is required for virulence (Bacon, et al., Mol. Microbiol. 40:769-777 (2001)). More recently, polysaccharide capsule conjugated to a protein carrier has been shown to protect non-human primates against diarrheal disease (Monteiro, et al., Infect Imm. 77(3): 1128-36 (2009)). Differentiation of *Campylobacter jejuni* strains is typically conducted through the use of Penner serotyping.

The Penner or "heat stable" serotyping scheme is a passive slide hemaglutination assay for both *C. jejuni* and *C. coli* that includes 47 *C. jejuni* serotypes. Rabbit polyclonal antibodies are generated against whole cells of each of the 47 type strains. Antigens are extracted from *C. jejuni* strains to be tested by heating bacterial suspensions in saline at 100° C. These "heat-stable" antigens are used to sensitize sheep erythrocytes, which are used in a passive slide hemagglutination assay with the specific polyclonal antisera. Genetic studies indicate that CPS is the major serodeterminant of the Penner scheme. Thus, mutation of genes required for CPS biogenesis rendered many strains un-typable in the Penner scheme.

However, other surface heat stable surface structures such as lipooligosaccharides (LOS) may also contribute to serospecificity of some Penner types. The capsular polysaccharides of *C. jejuni* are known to be structurally diverse (Karlyshev et al., *Molecular Microbiology* 55:90-103) (2005)). This structural diversity is consistent with the variability observed in the genes encoding the capsule in *C. jejuni*. The capsule locus of *C. jejuni* includes both highly conserved genes involved in capsule synthesis and highly variable loci that encode genes involved in synthesis of specific sugars and specific glycosyl transferases required to link the sugars together. The variable CPS locus located between two conserved genes, kpsC and kpsF, and the variable genes can range from 15 to 34 kb (FIG. 1). Variable genes also encode synthesis and transfer of modifications to the sugars, such as methyl phosphormidate (MeOPN) (Karlyshev et al., *Molecular Microbiology* 55:90-103).

Penner serotyping is technically difficult to perform and expensive to produce the type antisera. As a result, only a handful of reference laboratories routinely perform Penner typing. Moreover, many serotypes fall into Penner "complexes". The significance of these complexes is not totally understood in most cases, but they appear to include capsules with related structures (Aspinall, et al. *Carbohydr Res.* 231: 13-30 (1992)).

Others have tried to replace the laborious Penner serotyping using a molecular typing approach involving restriction fragment length polymorphism (RFLP) analysis of PCR amplified lipooligosaccharide (LOS) loci (Shi et al. *J Clin Microbiol.* 40(5):1791-7 (2002); Nakari et al., *J Clin Microbiol.* 43(3):1166-70) (2005)). However, these RFLP methods have not been widely used and have not replaced Penner serotyping as the typing method of choice. This may be due in part to the RFLP method requiring amplification of a 9.6kb fragment. Using PCR to generate such large amplicons is difficult and can place special requirements on the PCR conditions and reagents used, as demonstrated by Nakari et al., who were unable to generate amplified fragments using the amplification conditions described by Shi, et al. These RFLP methods are also limited because they are based on the amplification of the LOS locus. At the time of the Shi et al. study, it was known that both the LOS and CPS structure were part of the Heat Stable antigen (HS) recognized through the Penner serotyping method. However, in 2005, CPS was demonstrated to be the major serodeterminant of the Penner method (Karylshev, et al., Mol. Micro. 55: 90-103 (2005)). This helps explain why Shi et al. and Nakari et al. found only partial correlation between the Penner serotypes and RFLP groups. Penner serotyping distinguishes strains that cannot be distinguished by this RFLP method. For example, the most common RFLP type, Hh1Dd1, contained strains belonging to several HS serotypes, including HS 6,7, HS 12, HS 27, HS 55, HS 21, HS 10, HS 57, HS 6, HS 15, HS 23,36,53, and HS 27+HS 31 (Nakari et al., *J Clin Microbiol.* 43(3):1166-70 (2005)). And some serotypes, such as HS 2, HS 3, HS 4 complex, HS 8, HS 10, HS 11, HS 12, HS 15, HS 19, HS 31, HS 32, HS 41, HS 57, and HS 23,36,53 include more than one RFLP (Nakari et al., *J Clin Microbiol.* 43(3):1166-70 (2005)).

SUMMARY OF THE INVENTION

The current invention relates to reagents and method to identify *Campylobacter jejuni* Capsule/Penner types via molecular, rather than serological, methods.

Therefore, an object of the invention is a panel of multiplex DNA primers for identification of *C. jejuni* Capsule/Penner types by polymerase chain reaction (PCR).

Several important advantages of amplification reactions over serological determination are evident. First, it is technically difficult to perform and expensive to produce type antisera. As a result, few reference laboratories are capable of routine Penner typing. Additionally, many serotypes fall into Penner "complexes."

Amplification methods, unlike typing sera methods, are relatively available to research and reference laboratories. Furthermore, no expression of capsule is needed. Therefore, there are no affects due to phase variation in capsule expression, as is possible with serotyping. Multiplexing reduces the number of reactions to be performed per samples. Additionally, amplification reactions do not suffer from CPS being shut down or modified thru slipstrand mutations. The instant invention can identify 23 serotypes.

The multiplex amplification technique amplifies a fragment less than 1 kb that can be routinely performed in any molecular biology lab worldwide.

DETAILED DESCRIPTION OF PREFERRED EMBODIMENTS

The following terms are defined:

"Amplification reaction" refers to a method of detecting target nucleic acid by in vitro amplification of DNA or RNA.

"Polymerase chain reaction (PCR)" refers to the amplification of a specific DNA sequence, termed target or template sequence, that is present in a mixture, by adding two or more short oligonucleotides, also called primers, that are specific for the terminal or outer limits of the template sequence. The template-primers mixture is subjected to repeated cycles of heating to separate (melt) the double-stranded DNA and cooling in the presence of nucleotides and DNA polymerase such that the template sequence is copied at each cycle.

"Primer" refers to DNA oligonucleotides complementary to a region of DNA and serves as the initiation of amplification reaction from the 5' to 3' direction.

"Primer pair refers to the forward and reverse primers in an amplification reaction leading to amplification of a double-stranded DNA region of the target. PCR primer "mix" is defined as the forward and reverse primer pairs for specific targets, whereby the products within the "mix" differ by at least 20 bp.

"Target" refers to a nucleic acid region bound by a primer pair that is amplified through an amplification reaction. The PCR "product" or "amplicon" is the amplified nucleic acid resulting from PCR of a set of primer pairs.

The term "multiplex amplification reaction" herein refers the detection of more than one template in a mixture by the addition of more than one set of oligonucleotide primers. In a preferred embodiment, primer pairs are grouped into "mixes" to ensure ready detection of PCR products.

The term "capsule" herein refers to the structure lying outside the cell wall of bacteria, such as *Campylobacter jejuni*.

Utilizing genomic and capsule loci sequences, a molecular method for determining Penner and capsule type was developed. This method is simpler than Penner serotyping. The inventive method is more easily standardized than Penner serotyping, since molecular reagents (i.e., primers) can be produced and standardized resulting in lower cost. Additionally, the method does not require that the capsule be expressed. Therefore, it is not affected by phase variation in capsule expression, unlike the typing system.

In one embodiment, the current invention provides a method to specifically distinguish specific *C. jejuni* strains and recognize Capsule/Penner serotypes thru PCR amplification of type specific sequences. The inventive method and reagents permit identification of *Campylobacter jejuni* Penner types without the potential for capsule shutdown or modification due to slip-strand mutations.

EXAMPLE 1

PCR Primers Correlating to Penner Serotype

Figure 1:
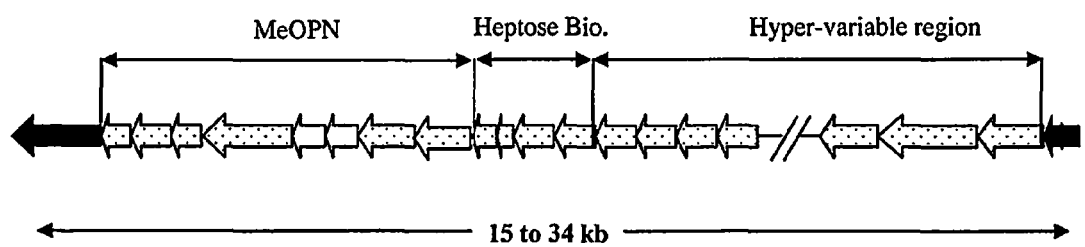
FIG. 1. Schematic of the general organization of the capsule loci of *C. jejuni*. The region between kpsC and kpsF (black arrows) encodes the genes for synthesis of distinct capsule structures. If present, genes for heptose and MeOPN synthesis are highly conserved. The region to the right is the hyper-variable region containing sugar transferases and sugar biosynthetic genes.

The capsule locus of *C. jejuni* includes both highly conserved genes involved in capsule synthesis and highly variable loci that encode genes involved in synthesis of specific sugars and specific glycosyl transferases required to link the sugars together. The variable CPS locus, located between two conserved genes, kpsC and kpsF, and the variable genes range from 15 to 34 kb (FIG. 1). Variable genes also encode synthesis and transfer of modifications to the sugars, such as methyl phosphoramidate (Karlyshev, A. et al., Mol. Microbiol. 55:90-103 (2005)). In a preferred embodiment, based on the DNA sequences, unique DNA sequences from the capsule loci (FIG. 1) of *C. jejuni*, for each Penner type, were identified. The selected genes were further compared to the whole genome sequences of *C. jejuni* in order to eliminate potential similarities with genes outside the CPS region.

Selection of genes unique to a particular serotype was performed using a local BLAST program. Each single gene of the variable capsule region (between kpsC and kpsF) was compared with a database containing the nucleotides sequences of all the available capsule loci of *C. jejuni*. The selected genes were further compared to the whole genome sequences of *C. jejuni* sequenced genomes to eliminate potential similarities with genes outside CPS region.

Multiplex primers were designed using PCR primers capable of correcting errors and closing gaps. Development of unique *Campylobacter jejuni* PCR primer sequences were undertaken by sequencing DNA of capsule loci derived from the strains: HS19, HS33, HS63, HS57, HS12, HS27, HS21, HS31, HS62, HS45, HS29, HS22, HS9, HS37, HS18, HS58, HS52, HS60, HS55, HS32, HS11, HS40, HS38, HS7, HS31, HS35, HS16, HS43, HS50, HS64 and HS65.

CPS sequencing strategies was undertaken within the conserved heptose genes hddA and dmhA region. If the strains to be sequenced produced a positive amplification with primers for hddA and dmhA, these genes were used as anchors for long-range PCR. This two-step PCR increased the probability of amplification by lowering the size of the PCR product. PCR amplifications were performed using a MASTER-AMP™ Extra-Long PCR kit from Epicentre (Madison, Wis.) or LONGAMP™ Taq DNA polymerases (New England Biolabs, Ipswich, Mass.). CPS locus sequences were obtained by cloning the kpsC-hddA and KpsF-dmhA PCR fragments into a pCR4-TOPO™ vector (Invitrogen, Carlsbad, Calif.) in order to create a representative genomic library. Following purification, clones were sequenced. Assembly was performed using SEQUENCHER® 4.8 (Gene Codes Corporation, Ann Arbor, Mich.).

A database of CPS loci was created to identify unique regions of each serotype. PCR primers, using online software, were designed with the following parameters: length between 18 and 30 residues, 20 to 50% GC content, and melting temperature ranging from 57 to 63° C. The primer sequences were verified for absence of dimerization or hairpin formation using AUTODIMER™ (Vallone and Butler, Biotechniques 37(2): 226-231 (2004)). The PCR primer sets (i.e., forward and reverse primers) were grouped into multiple mixes so that each group or mix produced amplicons that differ by at least 20 bp from the other amplicons in the same group or mix.

The forward and reverse primers are shown in Table 1, along with the associated sequence identity number (SEQ ID No.). The primers were designed within genes within the CPS loci and are summarized in Table 1. Table 1 identifies the sequence identification numbers (SEQ ID No.) of the forward and reverse primers along with the product size.

TABLE 1

| | PCR Product size (bp) | Penner type identified | Designed in Gene (function) | Forward primer (SEQ ID No.) | Reverse primer (SEQ ID No.) | PCR Product SEQ ID No. |
|---|---|---|---|---|---|---|
| Mix Alpha | | | | | | |
| Mu_HS19 | 450 | HS19 | HS19.07 (MeOPN transferase) | 1 | 2 | 47 |
| Mu_HS63A | 522 | HS63 | HS63.23 (glycosyl transferase) | 3 | 4 | 48 |
| Mu_HS33A | 819 | HS33 and HS35 | HS33.07 (MeOPN transferase) | 5 | 6 | 49 |
| Mix Beta | | | | | | |
| Mu_HS57 | 100 | HS57 | HS57.02 (Unknown) | 7 | 8 | 50 |
| Mu_HS12D | 201 | HS12 | HS12.15 (glycosyl transferase) | 9 | 10 | 51 |
| Mu_HS27A | 280 | HS27 | HS27.12 (sugar transferase) | 11 | 12 | 52 |
| Mu_HS21A | 801 | HS21 | HS21.05 (NAD-dep. epimerase/dehydratase) | 13 | 14 | 53 |
| Mu_HS31 | 857 | HS31 | HS31 17-18 (RmlD (RmlD substrate binding domain protein) | 15 | 16 | 54 |
| Mix Gamma | | | | | | |
| Mu_HS62 | 82 | HS62 | HS62.09 (Unknown) | 17 | 18 | 55 |
| Mu_HS45A | 128 | HS45 | HS45.10 (dmhA) | 19 | 20 | 56 |
| Mu_HS29A | 185 | HS29 | HS29.07 (MeOPN transferase) | 21 | 22 | 57 |
| Mu_HS22G | 216 | HS22 | HS22.08 (sugar transferase) | 23 | 24 | 58 |
| Mu_HS9A | 278 | HS9 | HS9.08 (sugar transferase) | 25 | 26 | 59 |
| Mu_HS37 | 541 | HS37 | HS37.28 | 27 | 28 | 60 |
| Mu_HS18A | 653 | HS18 | HS18.07 | 29 | 30 | 61 |
| Mix Delta | | | | | | |
| Mu_HS58C | 85 | HS58 | HS58.13 (sugar transferase) | 31 | 32 | 62 |
| Mu_HS52C | 170 | HS52 | HS52.07 (MeOPN transferase) | 33 | 34 | 63 |
| Mu_HS60A | 241 | HS60 | HS60.14 (Unknown) | 35 | 36 | 64 |
| Mu_HS55B | 341 | HS55 | HS55.06 (Unknown) | 37 | 38 | 65 |
| Mu_HS32A | 420 | HS32 | HS32.18 (GDP-fucose protein O-fucosyltransferase) | 39 | 40 | 66 |
| Mu_HS11D | 540 | HS11 | HS11.11 (Unknown) | 41 | 42 | 67 |
| Mu_HS40C | 636 | HS40 | HS44.13 (transketolase) | 43 | 44 | 68 |
| Mu_HS38B | 741 | HS38 | HS38.05 (CMP-KDO synthetase) | 45 | 46 | 69 |

Comparison of CPS loci resulted in confirmation that the relation between strains belonging to the same complex had similar CPS loci. For example, the strain HS33 CPS loci is highly similar to HS35. No difference of CPS sequence was identified between these serotypes. As such, PCR primers that identify HS33 also identify HS35 and HS33/35 strains (i.e., defined as the HS33 complex). Similarly, HS5 is highly similar to HS31, with no difference of CPS sequence identified between theses serotypes. Consequently, HS5 and HS31 are also associated using Penner serotyping. Therefore, PCR primers that identify HS31 also identify HS5 and HS5/31 strains (i.e., defined as the HS5 complex). Also, HS6 is similar to HS7. HS6 and HS7 are also associated using Penner serotyping. No difference in CPS nucleotide sequence was found between these serotypes. As such, Mu_HS6 primers identify HS6, HS7 and HS6/7 strains (defined as HS6 complex).

EXAMPLE 2

Multiplex PCR Assay

In a preferred embodiment, PCR primers were designed in regions that were found unique to each particular *C. jejuni* serotype. In a preferred embodiment, the PCR primers were designed to permit multiplex PCR. Multiplex PCR significantly reduces the number of reactions needed for strain identification. Design of the multiplex primers was conducted utilizing the online software MUPLEX™ (Boston University, Boston, Mass.) (described in Rachlin, et al., Nucleic Acid Research 33 (Web Server Issue): W544-W547) (2005).

In one embodiment, primer sets are grouped into multiple "mixes" based on the sizes of the products amplified. The amplified products (i.e., amplicons) for each primer pair is shown in Table 1, along with the associated sequence identification number (SEQ ID NO.). In a preferred embodiment, amplification and identification of *C. jejuni* strains is conducted utilizing four (4) "mixes" or groupings: (alpha) α; (beta) β; (gamma) γ; and (delta) Δ mixes, although other potential groupings or mixes are contemplated. The "mixes" or groupings of primer pairs, along with the associated *C. jejuni* strain(s), in the preferred embodiment, is illustrated in Table. 1. In Table 1, the alpha mix contains primers that distinguish HS19, HS63, and HS33/HS35. The beta mix contains PCR primers that distinguish HS57, HS12D, HS27A HS21A and HS31. The gamma mix contains primers that can distinguish strains HS62, HS45, HS29, HS22, HS9, HS37 and HS18. The delta mix contains PCR primers that can distinguish *C. jejuni* strains HS58, HS52, HS60, HS55, HS32, HS11, HS40 and HS38.

Primers were evaluated for their ability to enable efficient amplification of *C. jejuni* target DNA, resulting in a predicted product and for not interfering with other primers included in the reaction. The primer sets for a given "mix" were designed to produce amplicons that differ by at least 20 bp from the other amplicons in the same mix. Primer sets were judged satisfactory if they produced the expected size PCR product on their Penner serotype DNA template or related complexes and were negative for other tested serotypes. A positive control is also included to control assay operation and to evaluate whether the samples are derived from *C. jejuni*. The positive control is included in the "mix" that, like the other primer pairs, results in a difference of at least 20 bp from the other primers. In a preferred embodiment, the control are IpxA primer sets, although other controls are contemplated.

Although other potential PCR parameters are contemplated, in a preferred embodiment, the PCR amplification of *C. jejuni* samples comprises the following steps:
  a. Obtain a sample suspected of containing *Campylobacter jejuni* DNA;
  b. Subject sample containing said DNA to one or more of the primer pairs listed in Table 1, or a primer pair capable of amplifying the same product shown in Table 1. In a preferred embodiment, the primers are 18-30 nucleotides, have a G/C content of 20-50%, and a melting temperature between about 57° C. and 63° C.;
  c. Amplify target DNA under the following parameters: 94° C. for 30", 56° C. for 30", 72° C. for 45" for a total of 29 cycles;
  d. Subsequent to PCR amplification compare PCR product size.

Amplifying DNA from an unknown *C. jejuni* sample, using the primers in Table 1, and comparing the size of the ensuing amplification products permits identification of *C. jejuni* Penner serotypes. In a preferred embodiment, the amplified DNA is separated and sized. In one embodiment, sizing is through an agarose gel (2%), run in 0.5×TBE buffer. The sizes of the PCR products and corresponding serotype are determined by comparison with 100 bp molecular size standards. In a preferred embodiment, a positive control is included. As an example, primers to the gene IpxA is used as a control. In a preferred embodiment, the IpxA control is included in the gamma (γ) mixture to ensure the easiest visualization of the predicted 331 bp product. If the sample was derived from *C. jejuni*, a 331 bp product should be observed. If no 331 product is obtained, then errors were made in the application of the assay method or the sample is not derived from *C. jejuni*. Although agarose gel electrophoresis is a preferred method, other methods to analyze PCR product size are contemplated.

Figure 2:
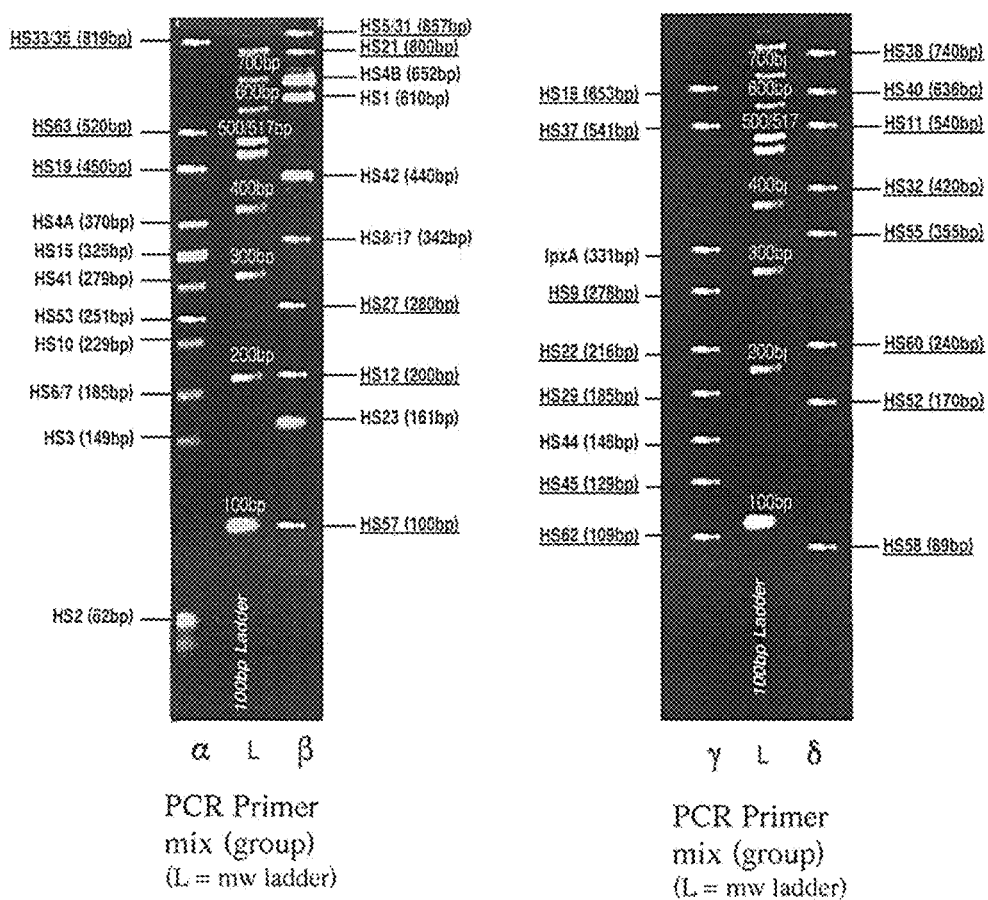
FIG. 2. Predicted product size for amplicons. Amplified DNA is separated and sized through an agarose gel (2%), run in 0.5×TBE buffer. The underlined products are those defined by the primers in this current application. The other products are identified by the PCR primers in U.S. patent application Ser. No. 13/031,718, filed 22 Feb. 2011, to which this application claims priority.

FIG. 2 illustrates the product migration by agarose gel electrophoresis (2% agarose) and the associated strains. The capsule loci sequences obtained were then compared to Penner serotyping results. The predicted PCR product size, for a given "mix" and associated Penner serotype is illustrated in the results shown in FIG. 2. In the example illustrated in FIG. 2, the primers are grouped into an α, β, γ, and Δ "mix", based on achieving at least 20 bp difference between the PCR products, in order to easily distinguish products.

In other embodiments, methods are carried out, at least in part, using a solid support. A variety of different supports can be used. In some embodiments, the solid support is a single solid support, such as a chip or wafer, or the interior or exterior surface of a tube, cone, plastic plate or other article. In some embodiments, the solid support is a particulate support, also referred to as a microsphere, bead or particle. Typically, the particles form groups in which particles within each group have a particular characteristic. Examples of suitable characteristics include, but are not limited to, color, fluorescence frequency, density, size, or shape. The selection of characteristics will depend on multiple criteria including the ability to distinguish or separate target-bound particles from particles of other groups. Particles can be separated by a number of methods. In a preferred embodiment, the particles can be separated using techniques, such as, for example, flow cytometry.

The particles can be fabricated from virtually any insoluble or solid material. For example, the particles can be fabricated from silica gel, glass, nylon, resins, SEPHADEX™, SEPHAROSE™, cellulose, magnetic material, a metal (e.g., steel, gold, silver, aluminum, copper, or an alloy) or metal-coated material, a plastic material (e.g., polyethylene, polypropylene, polyamide, polyester, polyvinylidenefluoride (PVDF)) and the like, and combinations thereof. Examples of suitable micro-beads are described, for example, in U.S. Pat. Nos. 5,736,330, 6,046,807 and 6,057,107, all of which are incorporated herein by reference in their entirety.

Thus, in one embodiment, the multiplex method described herein is performed using microspheres conjugated to unique capture oligonucleotides, permitting the analysis of many different nucleic acids in a single reaction. Each unique capture oligonucleotide is complementary to a unique tag sequence within one of the amplicons to be detected. In this embodiment, the microsphere mix consists of a number of microspheres equal to the number of serotypes that can be detected in the assay. Each of the microspheres contains a different fluorescent dye mix and is coupled to a unique capture oligonucleotide sequence complementary to a unique tag sequence within the amplicon of each serotype of interest. The hybridization of the capture oligonucleotide and the tag sequence of an amplicon results in the coupling of the amplicon to the solid support. The unique capture oligonucleotide and its complementary tag sequence are, thus, associated with a single, specific Penner serotype. The capture oligonucleotides are designed so there is no cross-hybridization between the capture oligonucleotides and the amplicons from more than one serotype under the hybridization conditions used.

In this method, the multiplex primer sets are used to amplify regions of interest in a *C. jejuni* DNA sample in the presence of a biotinylated dNTP mixture. Instead of running the amplified PCR fragments on an agarose gel to estimate their size, the amplified PCR fragments are incubated with microspheres conjugated to capture oligonucleotides specific for the serotypes of interest and streptavidin conjugated to a dye, such as phycoerythrin, and analyzed using an appropriate detection system.

Having described the invention, one of skill in the art will appreciate in the appended claims that many modifications and variations of the present invention are possible in light of the above teachings. It is therefore, to be understood that, within the scope of the appended claims, the invention may be practices otherwise than as specifically described.

What is claimed is:

1. A method of identifying *Campylobacter jejuni* strains in a sample suspected of containing *Campylobacter jejuni* DNA by polymerase chain reaction, wherein the amplification products of said polymerase chain reaction are derived from genes within the *Campylobacter jejuni* polysaccharide capsule (CPS) loci, comprising: (a) subjecting DNA from said sample to a PCR amplification reaction using one or more PCR primer pairs targeting one or more regions of the *C. jejuni* O-methyl phosphoramidate synthesis region, heptose synthesis and hyper-variable region of the *Campylobacter jejuni* polysaccharide capsule loci; (b) analyzing amplification products resulting from said amplification reaction, wherein said polysaccharide capsule loci is derived from *Campylobacter jejuni* strains selected from the group consisting of HS19, HS63, HS33, HS35, HS57, HS12, HS27, HS21, HS31, HS62, HS45, HS29, HS22, HS9, HS37, HS18, HS58, HS52, HS60, HS55, HS32, HS11, HS40, and HS38.

2. The method of claim 1, wherein said amplification products are analyzed by size determination.

3. The method of claim 1, wherein said PCR primer pairs contain sequences selected from the group consisting of: SEQ ID No. 1 and SEQ ID No. 2; SEQ ID No. 3 and SEQ ID No. 4; SEQ ID No. 5 and SEQ ID No. 6; SEQ ID No. 7 and SEQ ID No. 8; SEQ ID No. 9 and SEQ ID No. 10; SEQ ID No. 11 and SEQ ID No. 12; SEQ ID No. 13 and SEQ ID No. 14; SEQ ID No. 15 and SEQ ID No. 16; SEQ ID No. 17 and SEQ ID No. 18; SEQ ID No. 19 and SEQ ID No. 20; SEQ ID No. 21 and SEQ ID No. 22; SEQ ID No. 23 and SEQ ID No. 24; SEQ ID No. 25 and SEQ ID No. 26; SEQ ID No. 27 and SEQ ID No. 28; SEQ ID No.29 and SEQ ID No. 30; SEQ ID No. 31 and SEQ ID No. 32; SEQ ID No. 33 and SEQ ID No. 34; SEQ ID No. 35 and SEQ ID No. 36; SEQ ID No. 37 and SEQ ID No. 38; SEQ ID No. 39 and SEQ ID No. 40; SEQ ID No. 41and SEQ ID No. 42; SEQ ID No. 43 and SEQ ID No. 44; and SEQ ID No. 45 and SEQ ID No. 46.

4. The method of claim 1, wherein said PCR reaction is multiplex amplification reaction.

5. The method of claim 1, wherein said primers are grouped in an alpha mix and a beta mix with the alpha and beta mixes that are separately added to an unknown DNA sample in order to discriminate product sizes.

6. The method of claim 1, wherein said sample is a clinical sample.

7. The method of claim 1, wherein said sample is collected from a matrix selected from the group consisting of a bacterial culture, a blood, a tissue, and fecal material.

8. The method of claim 1, wherein the primers have about 18-30 nucleotides, a G/C content of 20-50%, and a melting temperature between about 57° C. and 63° C.

9. The method of claim 1, wherein said amplification reaction yields one or more amplification products selected from the group consisting of SEQ ID No. 47;

SEQ ID No. 48; SEQ ID No. 49; SEQ ID No. 50; SEQ ID No. 51; SEQ ID No. 52; SEQ ID No. 53; SEQ ID No. 54; SEQ ID No. 55; SEQ ID No. 56; SEQ ID No. 57; SEQ ID No. 58; SEQ ID No. 59; SEQ ID No. 60; SEQ ID No. 61; SEQ ID No. 62; SEQ ID No. 63; SEQ ID No. 64; SEQ ID No. 65; SEQ ID No. 66; SEQ ID No. 67; SEQ ID No. 68; and SEQ ID No. 69.

10. The method of claim 1, wherein said HS 19 PCR primers recognize HS19 Penner serotype; HS 63 PCR primers recognize HS63 Penner serotype; HS33 PCR primers recognize HS33 and HS35 Penner serotypes; HS57 PCR primers recognize HS57 Penner serotype; HS12 PCR primers recognize HS12 Penner serotype; HS27 PCR primers recognize HS27 Penner serotype; HS21 PCR primers recognize HS21 Penner serotype; HS31 PCR primers recognize HS31 Penner serotype; HS62 PCR primers recognize HS62 Penner serotype; HS62 PCR primers recognize HS62Penner serotype; HS45 PCR primers recognize HS45 Penner serotype; HS29 PCR primers recognize HS29 Penner serotype; HS22 PCR primers recognize HS22 Penner serotype; HS9 PCR primers recognize HS9 Penner serotype; HS37 PCR primers recognize HS37 Penner serotype; HS18 PCR primers recognize HS18 Penner serotype; HS58 PCR primers recognize HS58 Penner serotype; HS52 PCR primers recognize HS52Penner serotype; HS60 PCR primers recognize HS60 Penner serotype; HS55 PCR primers recognize HS55 Penner serotype; HS32 PCR primers recognize HS Penner serotype; HS11 PCR primers recognize HS11 Penner serotype; HS40 PCR primers recognize HS40 Penner serotype; and HS38 PCR primers recognize HS38 Penner serotype.

11. The method of claim 2, wherein the amplification of products are analyzed by agarose gel electrophoresis.

12. The method of claim 4, wherein said PCR primer pairs are grouped into an alpha mix; a beta mix; a gamma mix and a delta mix, wherein each of said mixes comprise PCR primer pairs so that each PCR product within a mix differs by at least 20bp.

* * * * *